(12) United States Patent
Takeuchi et al.

(10) Patent No.: US 10,798,972 B2
(45) Date of Patent: Oct. 13, 2020

(54) NON-BURNING TYPE FLAVOR INHALER

(71) Applicant: JAPAN TOBACCO INC., Tokyo (JP)

(72) Inventors: Manabu Takeuchi, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 101 days.

(21) Appl. No.: 15/881,410

(22) Filed: Jan. 26, 2018

(65) Prior Publication Data

US 2018/0146715 A1    May 31, 2018

Related U.S. Application Data

(63) Continuation of application No. PCT/JP2016/050699, filed on Jan. 12, 2016.

(30) Foreign Application Priority Data

Jul. 28, 2015 (WO) .................. PCT/JP2015/071346

(51) Int. Cl.
*A24F 47/00* (2020.01)
*A61M 15/06* (2006.01)
*H05B 3/44* (2006.01)

(52) U.S. Cl.
CPC ............ *A24F 47/008* (2013.01); *A24F 47/00* (2013.01); *A61M 15/06* (2013.01); *H05B 3/44* (2013.01)

(58) Field of Classification Search
None
See application file for complete search history.

(56) References Cited

U.S. PATENT DOCUMENTS 6,810,883 B2   11/2004 Felter et al.
9,072,321 B2    7/2015 Liu
(Continued)

FOREIGN PATENT DOCUMENTS

CN    203398241 U    1/2014
JP    2013-526834 A  6/2013
(Continued)

OTHER PUBLICATIONS

International Search Report, issued in PCT/JP2016/050699, PCT/ISA/210, dated Apr. 5, 2016.
(Continued)

*Primary Examiner* — Jacob T Minskey
*Assistant Examiner* — Baileigh Kate Darnell
(74) *Attorney, Agent, or Firm* — Birch, Stewart, Kolasch & Birch, LLP

(57) ABSTRACT

This non-combustion-type flavor inhaler is provided with: a housing having a housing cavity; an atomizer that atomizes an aerosol source without combustion; a control unit that controls at least the atomizer; a sensor that detects a change in the internal pressure in the housing cavity; a first structure that causes a change in the internal pressure in the housing cavity as a result of a suction action or a blowing action; and a second structure that causes a change in the internal pressure in the housing cavity as a result of a predetermined action other than the suction and blowing actions. The first structure comprises a mouthpiece opening provided at a mouthpiece end of the housing. The control unit performs atomization control to initiate or terminate atomization of the aerosol source on the basis of at least the suction action. The control unit performs predetermined control other than the atomization control on the basis of the predetermined action.

21 Claims, 10 Drawing Sheets

(56) References Cited

U.S. PATENT DOCUMENTS

| | | | | |
|---|---|---|---|---|
| 9,820,509 | B2* | 11/2017 | Newton | H05B 1/0244 |
| 9,913,494 | B2* | 3/2018 | Liu | A24F 47/008 |
| 2011/0278189 | A1* | 11/2011 | Terry | A24F 47/008 |
| | | | | 206/459.1 |
| 2012/0199663 | A1* | 8/2012 | Qiu | A61M 11/041 |
| | | | | 239/8 |
| 2013/0340775 | A1 | 12/2013 | Juster et al. | |
| 2014/0014126 | A1* | 1/2014 | Peleg | A24F 47/008 |
| | | | | 131/329 |
| 2014/0096782 | A1 | 4/2014 | Ampolini et al. | |
| 2014/0130797 | A1* | 5/2014 | Liu | A24F 47/008 |
| | | | | 128/202.21 |
| 2014/0332019 | A1* | 11/2014 | Liu | A61M 15/06 |
| | | | | 131/329 |
| 2014/0332022 | A1* | 11/2014 | Li | A24F 47/008 |
| | | | | 131/329 |
| 2014/0360516 | A1* | 12/2014 | Liu | A61M 15/06 |
| | | | | 131/329 |
| 2014/0366895 | A1* | 12/2014 | Li | H01M 2/1055 |
| | | | | 131/329 |
| 2015/0020831 | A1 | 1/2015 | Weigensberg et al. | |
| 2015/0047659 | A1 | 2/2015 | Liu | |
| 2015/0101625 | A1* | 4/2015 | Newton | H05B 1/0244 |
| | | | | 131/329 |
| 2015/0118895 | A1* | 4/2015 | Zheng | H01R 13/66 |
| | | | | 439/529 |
| 2015/0164142 | A1* | 6/2015 | Li | F22B 1/288 |
| | | | | 131/329 |
| 2016/0206005 | A1* | 7/2016 | Yamada | A24F 47/008 |

FOREIGN PATENT DOCUMENTS

| | | |
|---|---|---|
| JP | 2015-500647 A | 1/2015 |
| TW | I-306020 B | 2/2009 |
| WO | WO 2014/066730 A1 | 5/2014 |
| WO | WO 2014/150704 A2 | 9/2014 |
| WO | WO 2015/052513 A2 | 4/2015 |

OTHER PUBLICATIONS

Office Action issued in Taiwanese Patent Application No. 105123200 dated Oct. 24, 2017.
Extended European Search Report, dated Mar. 14, 2019, for European Application No. 16830075.4.
Chinese Office Action and Search Report for Chinese Application No. 201680044301.1, dated Oct. 11, 2019, with an English translation.
European Office Action for European Application No. 16830075.4, dated Apr. 15, 2020.

* cited by examiner

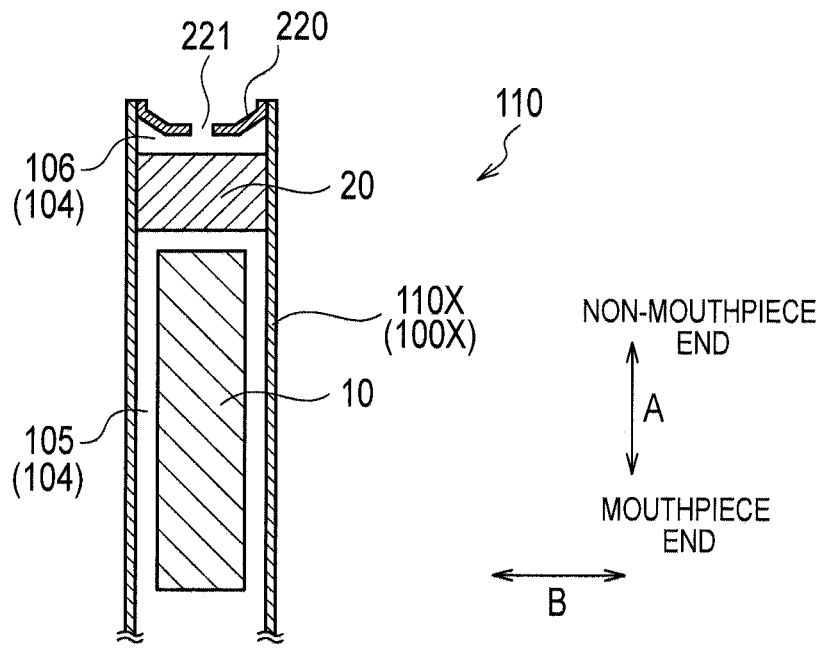
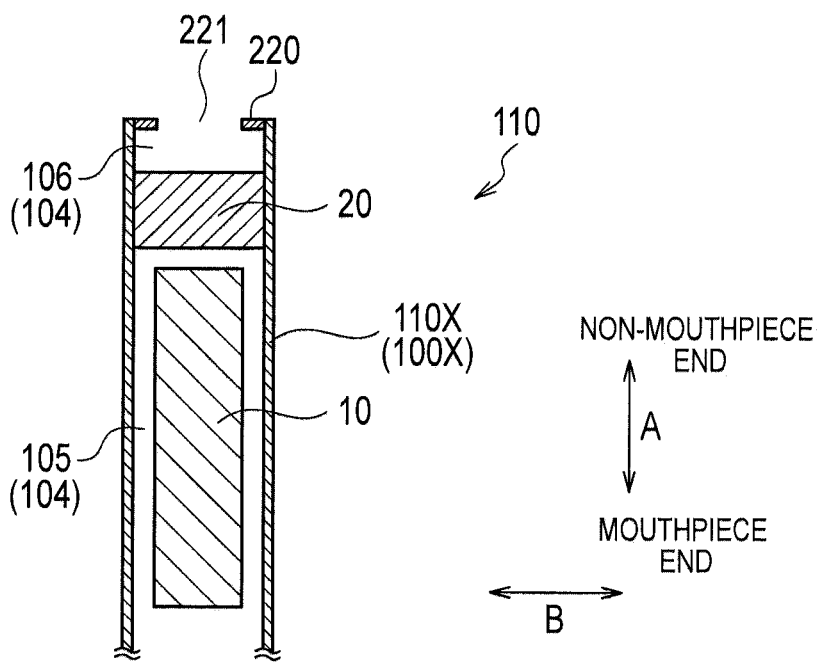

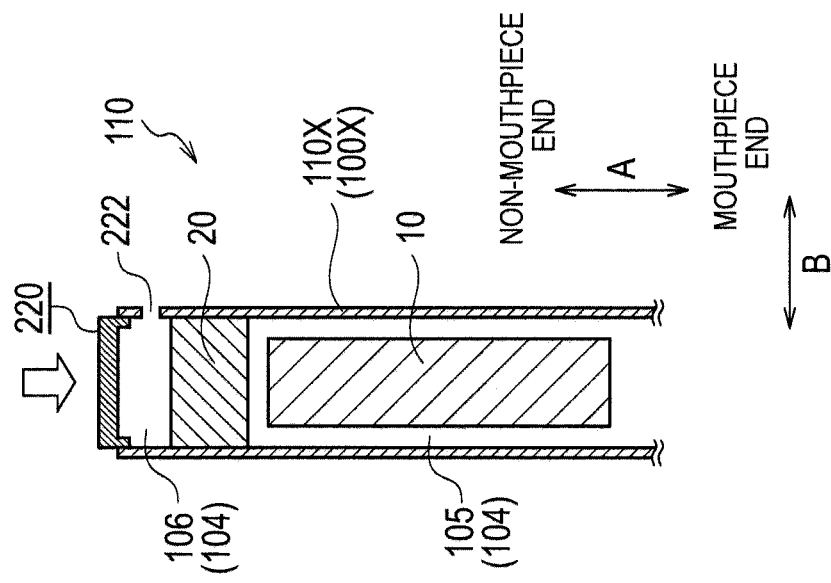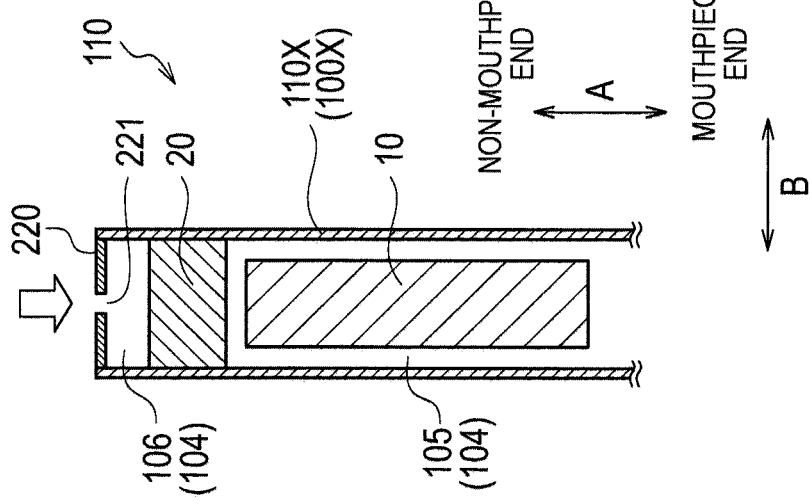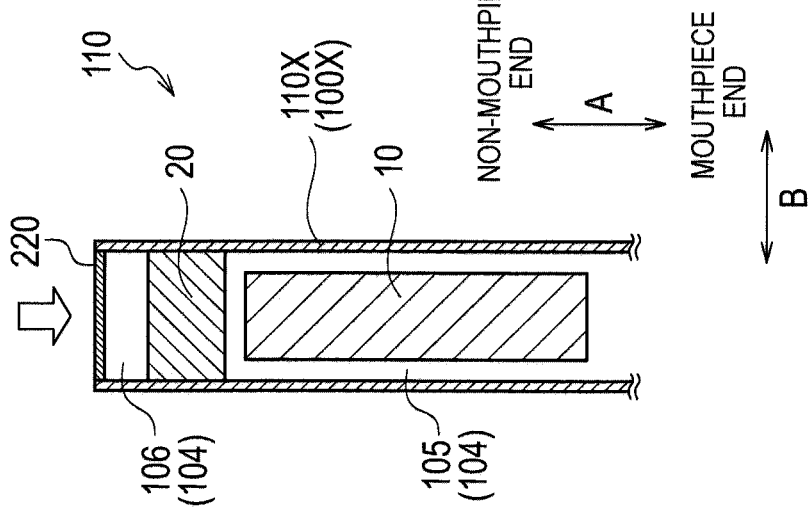

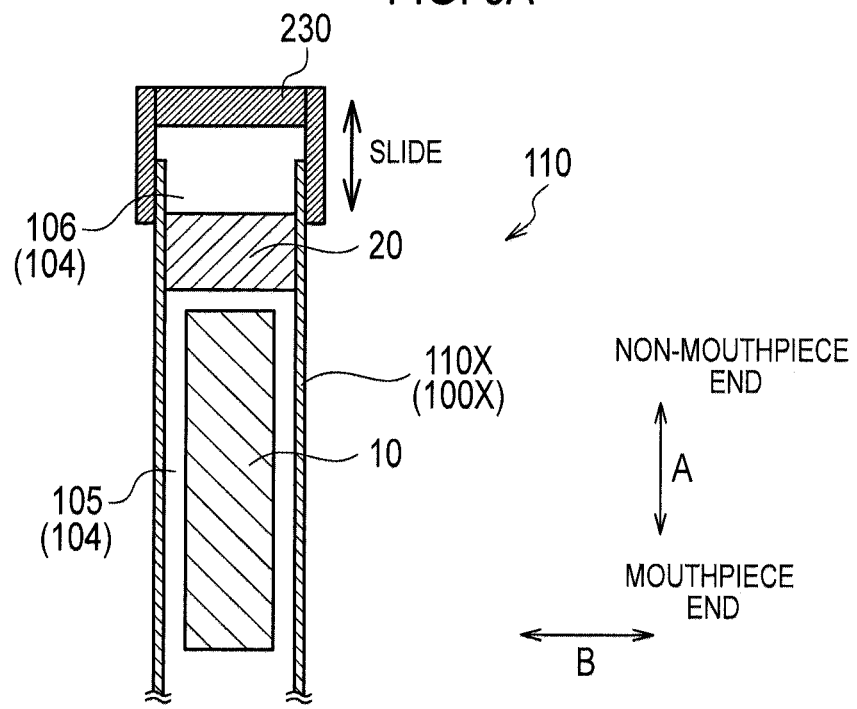
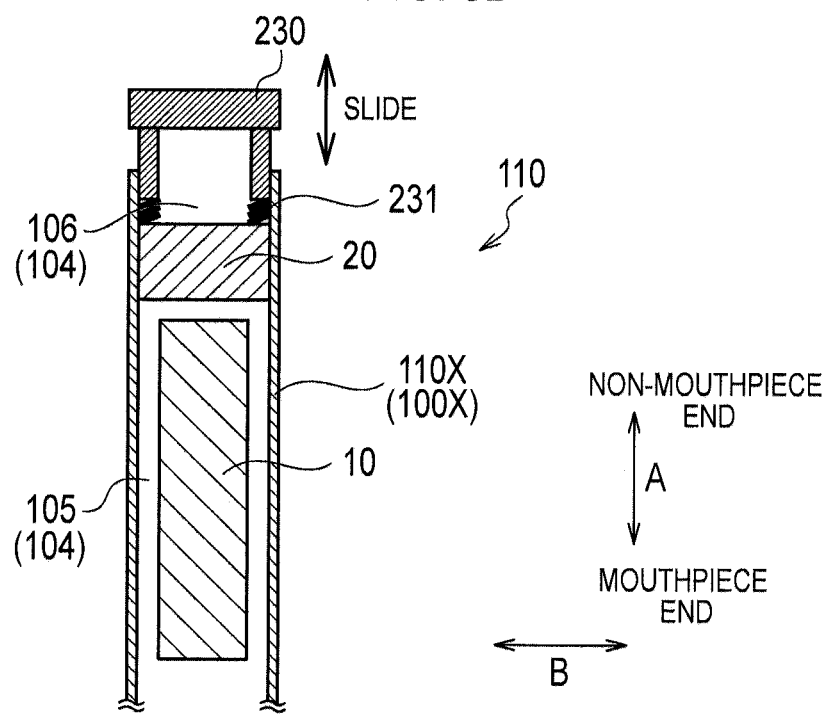

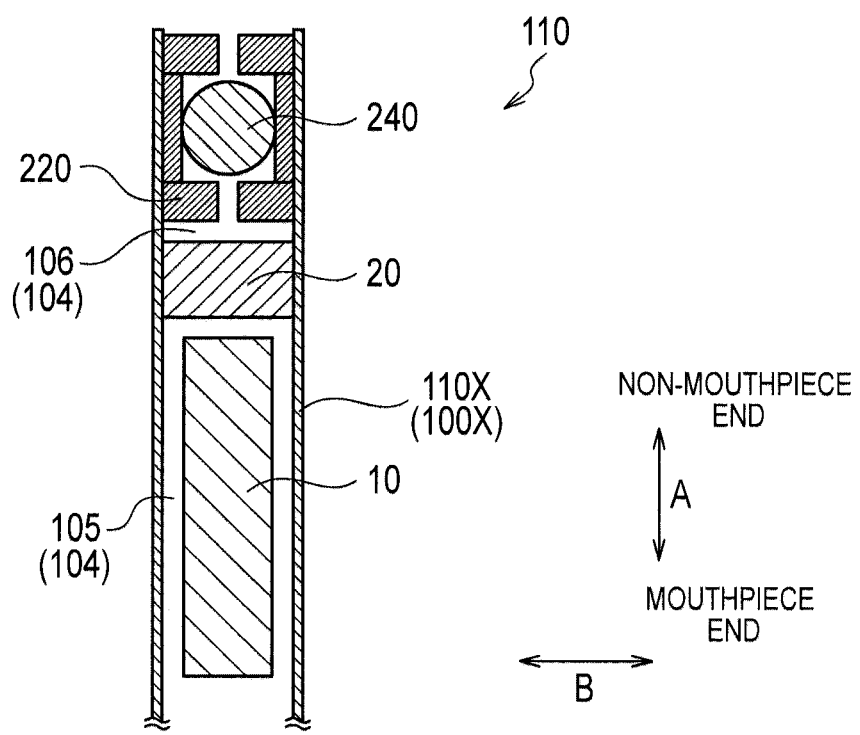

NON-BURNING TYPE FLAVOR INHALER

CROSS REFERENCE TO RELATED APPLICATIONS

This application is a Continuation of PCT International Application No. PCT/JP2016/050699 filed on Jan. 12, 2016, which claims priority under 35 U.S.C. § 119(a) to Patent Application No. PCT/JP2015/071346 filed in Japan on Jul. 28, 2015, all of which are hereby expressly incorporated by reference into the present application.

TECHNICAL FIELD

The present invention relates to a non-burning type flavor inhaler having an atomizer configured to atomize an aerosol source without burning.

BACKGROUND ART

Conventionally, a non-burning type flavor inhaler for inhaling flavor without burning has been known. The non-burning type flavor inhaler has an atomizer configured to atomize an aerosol source without burning.

With such a non-burning type flavor inhaler, it is preferred to be configured so that a power source output is supplied to the atomizer in an inhalation duration during which an inhalation action is performed, and a power source output is not supplied to the atomizer in a non-inhalation duration during which an inhalation action is not performed. To distinguish between such inhalation duration and non-inhalation duration, a sensor configured to detect the inhalation duration may be used. As such a sensor, it is possible to use a sensor configured to output a value that changes depending on an inhalation action (for example, Patent Literatures 1 and 2).

CITATION LIST

Patent Literature

Patent Literature 1: International Publication No. 2014/150704
Patent Literature 2: International Publication No. 2014/066730

SUMMARY OF THE INVENTION

A first feature is summarized as a non-burning type flavor inhaler comprising: a housing having a housing cavity; an atomizer configured to atomize an aerosol source without burning; a sensor configured to detect a change in inner pressure of the housing cavity; a controller configured to control at least the atomizer; a first configuration for changing the inner pressure of the housing cavity by an inhalation action or a blow action; and a second configuration for changing the inner pressure of the housing cavity by a predetermined action other than the inhalation action and the blow action, wherein the first configuration includes a mouthpiece aperture provided on a mouthpiece end of the housing, the controller is configured to perform an atomizing control for starting or terminating atomization of the aerosol source, based on at least the inhalation action, and the controller is configured to perform a predetermined control other than the atomizing control, based on the predetermined action.

A second feature according to the first feature is summarized as that the first configuration includes an aperture allowing for communication between the housing cavity and an aerospace outside the housing, and the aperture included in the first configuration communicates with the mouthpiece aperture.

A third feature according to the first feature or the second feature is summarized as that the second configuration has a configuration for increasing the inner pressure of the housing cavity by the predetermined action.

A fourth feature according to any one of the first to third features is summarized as that the first configuration, the second configuration, and the sensor are arranged in order of the second configuration, the sensor, and the first configuration, from a non-mouthpiece end side toward a mouthpiece end side of the housing.

A fifth feature according to any one of the first to fourth features is summarized as that the second configuration is provided at a non-mouthpiece end of the housing.

A sixth feature according to any one of the first to fifth features is summarized as that the housing cavity includes a first cavity communicating from the first configuration to the sensor and a second cavity communicating from the second configuration to the sensor, and the first cavity and the second cavity are partitioned not to communicate with each other within the housing.

A seventh feature according to any one of the first to sixth features is summarized as that an output value of the sensor is compared with a first threshold value to determine whether or not to perform the atomizing control of the atomizer and a second threshold value to determine the predetermined control other than the atomizing control of the atomizer, and
the first threshold value is larger than the second threshold value.

An eight feature according to the seventh features is summarized as that the second configuration has a configuration for changing the inner pressure of the housing cavity so that the output value of the sensor does not exceed the first threshold value and the output value of the sensor exceeds the second threshold value.

A ninth feature according to any one of the first to eight features is summarized as that the second configuration includes an aperture communicating from the housing cavity to the aerospace outside the housing.

A tenth feature according to the ninth features is summarized as that the aperture included in the second configuration is provided on an end surface of a non-mouthpiece end of the housing.

An eleventh feature according to the ninth features is summarized as that a first aperture and a second aperture are arranged as the aperture included in the second configuration, and the first aperture and the second aperture are provided on surfaces facing directions different from each other in the housing.

A twelfth feature according to the ninth features is summarized as that a first aperture and a second aperture are provided as the aperture included in the second configuration, the first aperture is provided on an end surface of a non-mouthpiece end of the housing, and the second aperture is provided on a side surface of the housing.

A thirteenth feature according to any one of the first to twelfth features is summarized as that the housing has a longer direction and a shorter direction perpendicular to the longer direction, and the second configuration is arranged not to protrude externally of an outer side surface of the housing in the shorter direction.

A fourteenth feature according to any one of the first to thirteenth features is summarized as that the second configuration is provided as a separate body from the housing.

A fifteenth feature according to any one of the first to fourteenth features is summarized as that a non-mouthpiece end of the housing is provided with an electrode member configured to charge a power source for supplying at least power to the atomizer, and the second configuration includes the electrode member.

A sixteenth feature according to the twelfth features is summarized as that the housing has a longer direction and a shorter direction perpendicular to the longer direction, and the electrode member has a first electrode and a second electrode.

A seventeenth feature according to the sixteenth features is summarized as that the electrode member includes an aperture allowing for communication between the housing cavity and an aerospace outside the housing, and the aperture included in the electrode member is provided to be closer to a mouthpiece end side, in the longer direction, than a non-mouthpiece side end of either one of the first electrode or the second electrode.

An eighteenth feature according to the sixteenth feature or the seventeenth feature is summarized as that the second electrode is spaced apart from the first electrode and provided internally of the first electrode, on a projection surface formed by light irradiated from the longer direction, the projection surface being formed on a surface perpendicular to the longer direction.

A nineteenth feature according to the eighteenth features is summarized as that the electrode member has an aperture, and the aperture is provided internally of the first electrode and externally of the second electrode, on the projection surface.

A twentieth feature according to any one of the first to nineteenth features is summarized as that a non-mouthpiece side end of the second electrode is provided to be closer to a mouthpiece end side than a non-mouthpiece side end of the first electrode, in the longer direction.

A twenty-first feature according to any one of the first to twentieth features is summarized as that the predetermined control is at least any one of: control for determining whether or not a user is an authorized user; control for starting or terminating a puff action series; control for switching an operation mode of the non-burning type flavor inhaler; control for resetting a value counted in the controller; and control for notifying a value managed by the controller.

The above-described characteristic may be summarized in that a non-mouthpiece end of the housing is provided with an endcap, and the second configuration includes the endcap.

The above-described characteristic may be summarized in that the endcap includes an aperture communicating from the housing cavity to an aerospace outside the housing.

The above-described characteristic may be summarized in that at least a part of the endcap is constituted of an elastic member.

The above-described characteristic may be summarized in that at least a part of the housing is constituted of an elastic member and the second configuration includes the elastic member.

The above-described characteristic may be summarized in that the housing includes a longer direction and a shorter direction perpendicular to the longer direction, a non-mouthpiece end of the housing is provided with a slide member constituted to be slidable along the longer direction, and the second configuration includes the slide member.

The above-described characteristic may be summarized in that the housing cavity is provided with a movable member constituted to be movable within the housing cavity, and the second configuration includes the movable member.

The above-described characteristic may be summarized in that the predetermined action is an action of blocking the aperture included in the second configuration with a hand finger cushion of a user.

The above-described characteristic may be summarized in that the predetermined action is an action for depressing the elastic member included in the second configuration.

The above-described characteristic may be summarized in that the predetermined action is an action for sliding the slide member.

The above-described characteristic may be summarized in that the predetermined action is an action for moving the movable member within the housing cavity.

The above-described characteristic may be summarized in that the housing includes a cylindrical shape or a rectangular tubular shape.

The above-described characteristic may be summarized in that the non-burning type flavor inhaler includes a light-emitting element configured to notify a state of the non-burning type flavor inhaler, and the light-emitting element is provided at a mouthpiece end side of the housing relative to the second configuration.

The above-described characteristic may be summarized in that the non-burning type flavor inhaler includes a light-emitting element configured to notify a state of the non-burning type flavor inhaler, and the light-emitting element is provided at a mouthpiece end side of the housing relative to the second cavity.

BRIEF DESCRIPTION OF THE DRAWINGS

FIGS. 5A and 5B are diagrams illustrating an electrical unit 110 according to a first modification.

FIGS. 6A-6C are diagrams illustrating the electrical unit 110 according to a second modification.

FIGS. 8A and 8B are diagrams illustrating the electrical unit 110 according to a fourth modification.

FIG. 9 is a diagram illustrating the electrical unit 110 according to a fifth modification.

DESCRIPTION OF EMBODIMENTS

Figure 1:
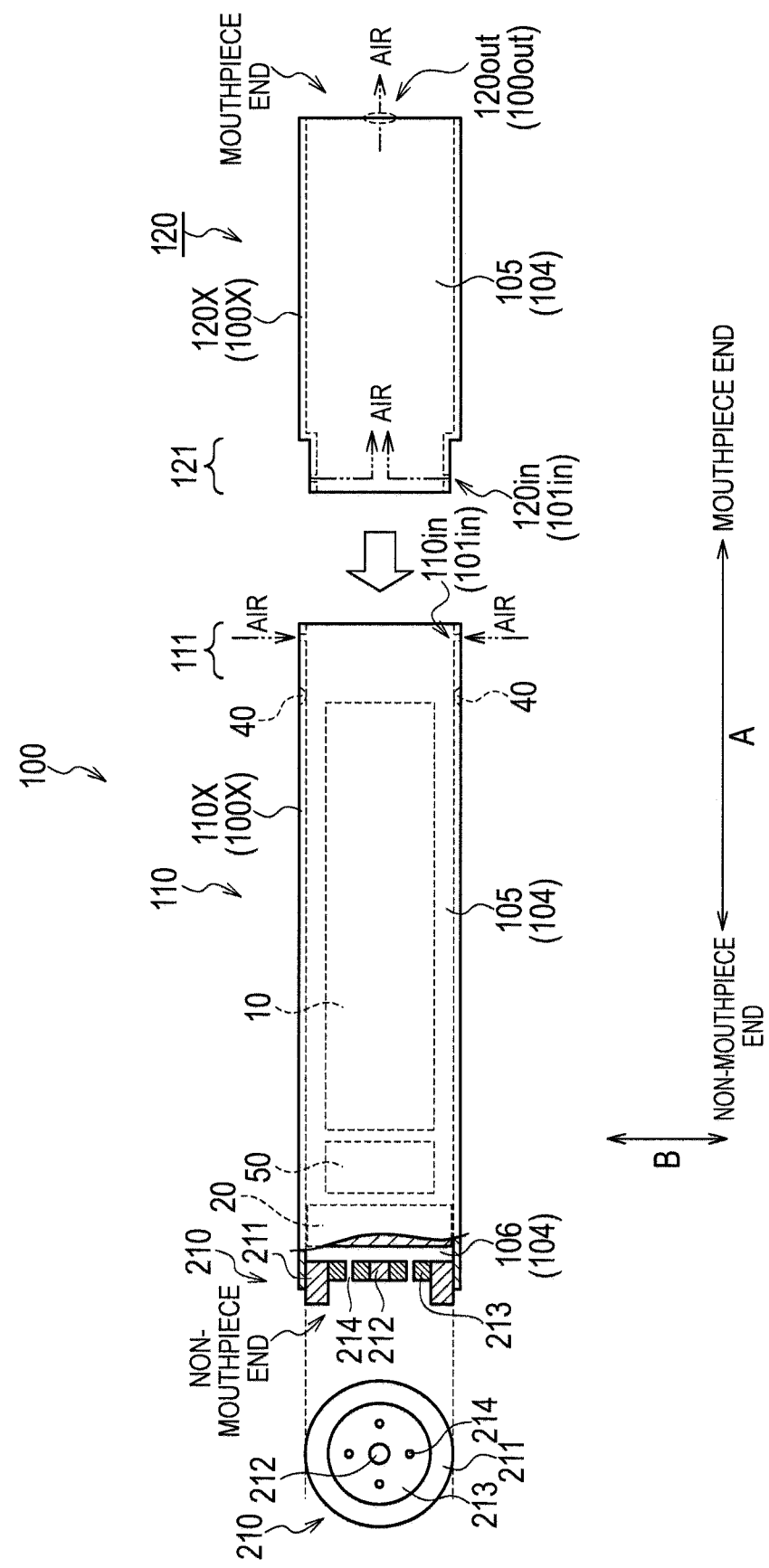
FIG. 1 is a diagram illustrating a non-burning type flavor inhaler 100 according to an embodiment.

Hereinafter, embodiments of the present invention will be described. In the following description of the drawings, the same or similar parts are denoted by the same or similar reference numerals. It is noted that the drawings are schematic, and the ratios of dimensions and the like may be different from the actual ones.

Therefore, specific dimensions and the like should be determined by referring to the following description. Of course, the drawings may include the parts with different dimensions and ratios.

Overview of Disclosure

The sensor mentioned in the BACKGROUND ART is used merely for detecting an inhalation duration (that is, atomizing control of an atomizer), and is not used for other uses. On the contrary, as a result of extensive studies, the inventors and others discovered that the sensor used for the atomizing control of the atomizer can be used for other uses.

A non-burning type flavor inhaler according to the overview of the disclosure comprises: a housing having a housing cavity; an atomizer configured to atomize an aerosol source without burning; a sensor configured to detect a change in inner pressure of the housing cavity; a controller configured to control at least the atomizer; a first configuration for changing the inner pressure of the housing cavity by an inhalation action or a blow action; and a second configuration for changing the inner pressure of the housing cavity by a predetermined action other than the inhalation action and the blow action, wherein the first configuration includes a mouthpiece aperture provided on a mouthpiece end of the housing, the controller is configured to perform an atomizing control for starting or terminating atomization of the aerosol source, based on at least the inhalation action, and the controller is configured to perform a predetermined control other than the atomizing control, based on the predetermined action.

In the overview of disclosure, a non-burning type flavor inhaler includes: a first configuration for changing an inner pressure of a housing cavity by an inhalation action or a blow action; and a second configuration for changing the inner pressure of the housing cavity by a predetermined action other than the inhalation action and the blow action, in which a sensor is configured to detect a change in the inner pressure of the housing cavity. According to such a constitution, as a member configured to detect a trigger for performing predetermined control different from the atomizing control for starting or terminating atomization of an aerosol source, the sensor used for the atomizing control is used, and thus, a wider range of usage of the sensor used for the atomizing control is realized. Further, if a trigger for performing a plurality of controls is detected by one sensor, it is also possible to decrease the number of components.

Embodiment

Non-Burning Type Flavor Inhaler

Figure 2:
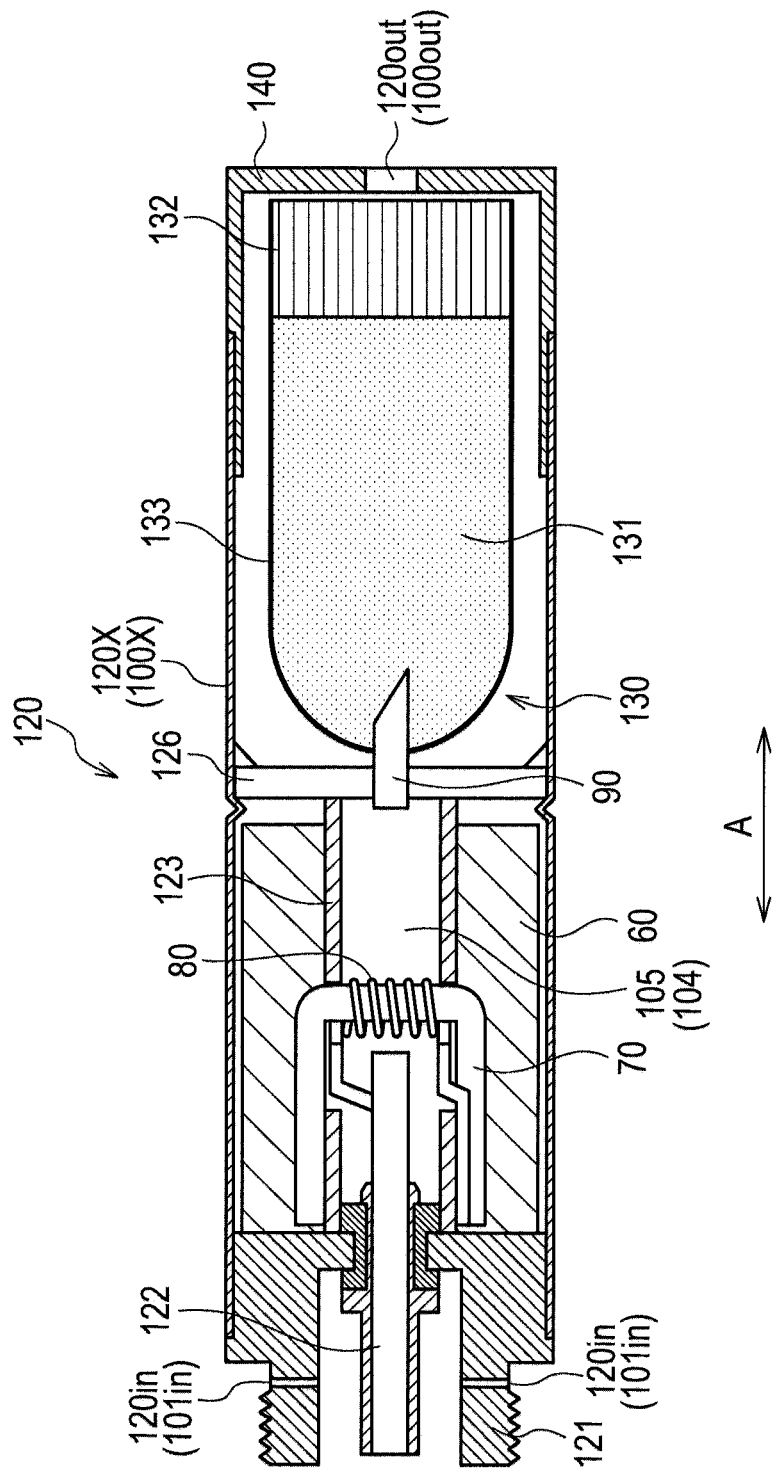
FIG. 2 is a diagram illustrating an atomizing unit 120 according to the embodiment.

A non-burning type flavor inhaler according to an embodiment will be described, below. FIG. 1 is a diagram illustrating a non-burning type flavor inhaler 100 according to the embodiment. FIG. 2 is a diagram illustrating an atomizing unit 120 according to the embodiment.

In the embodiment, the non-burning type flavor inhaler 100 is a device for inhaling flavor without burning, and has a shape extending along a longer direction A from a non-mouthpiece end side toward a mouthpiece end side.

As illustrated in FIG. 1, the non-burning type flavor inhaler 100 includes an electrical unit 110 and an atomizing unit 120. The electrical unit 110 has a female connector 111 at a site adjacent to the atomizing unit 120, and the atomizing unit 120 has a male connector 121 at a site adjacent to the electrical unit 110. The female connector 111 has a spiral groove extending along a direction perpendicular to the longer direction A, and the male connector 121 has a spiral projection extending along a direction perpendicular to the longer direction A. As a result of screwing of the female connector 111 and the male connector 121, the atomizing unit 120 and the electrical unit 110 are connected. The atomizing unit 120 is constituted to be removable with respect to the electrical unit 110.

In the embodiment, the non-burning type flavor inhaler 100 includes a housing 100X including a housing cavity 104. The housing cavity 104 includes a first cavity 105 provided at the mouthpiece end side relative to a sensor 20, and a second cavity 106 provided at the non-mouthpiece end side relative to the sensor 20. The housing 100X includes the longer direction A and a shorter direction B perpendicular to the longer direction A. The housing 100X preferably has a tubular shape such as a cylindrical shape or a rectangular tubular shape. The housing 100X includes a ventilation aperture 101in and a mouthpiece aperture 100out used at least for an inhalation action. The mouthpiece aperture 100out is provided at the mouthpiece end of the housing 100X, and the ventilation aperture 101in and the mouthpiece aperture 100out communicate with the first cavity 105.

Specifically, the electrical unit 110 includes an electrical housing 110X constituting a part of the housing 100X, and the electrical housing 110X includes an aperture 110in constituting a part of the ventilation aperture 101in. The atomizing unit 120 includes an atomizing housing 120X constituting a part of the housing 100X, and the atomizing housing 120X includes an aperture 120in constituting a part of the ventilation aperture 101in and an aperture 120out constituting the mouthpiece aperture 100out. The aperture 110in and the aperture 120in communicate with each other while the female connector 111 and the male connector 121 are connected.

Here, an end surface of the non-mouthpiece end of the housing 100X is provided with an electrode member 210 configured to charge a battery 10. The electrode member 210 includes a first electrode 211, a second electrode 212, an insulation member 213, and an aperture 214. The first electrode 211 and the second electrode 212 are connected with the battery 10, and are members for supplying power to the battery 10 by connecting an external power source and the battery 10. The second electrode 212 is spaced apart from the first electrode 211 yet provided internally of the first electrode 211, in a projection surface formed, by light irradiated from the longer direction A, on a surface perpendicular to the longer direction A. The non-mouthpiece side end of the second electrode 212 is provided to be closer to the mouthpiece end side than the non-mouthpiece side end of the first electrode 211, in the longer direction A. The insulation member 213 is a member for insulating the first electrode 211 and the second electrode 212. The aperture 214 communicating with the second cavity 106 is an aperture communicating from the housing cavity 104 (here, the second cavity 106) to an aerospace outside the housing 100X. In other words, the second cavity 106 communicates with the aerospace outside the housing 100X, via the aperture 214. The aperture 214 is provided internally of the first electrode 211 yet externally of the second electrode 212, on the projection surface. The aperture 214 is provided to be closer to the mouthpiece end side, in the longer direction A, than the non-mouthpiece side end of either one of the first electrode 211 or the second electrode 212 (here, the first electrode 211). It is noted that the electrode member 210 is provided on the end surface of the non-mouthpiece end of the housing 100X, and thus, it may be possible to consider that the aperture 214 is provided on the end surface of the non-mouthpiece end of the housing 100X.

In the embodiment, the ventilation aperture 101in and the mouthpiece aperture 100out constitute a first configuration for changing an inner pressure of the housing cavity 104 (here, the first cavity 105) by the inhalation action or a blow action. The electrode member 210 constitutes a second configuration for changing the inner pressure of the housing cavity 104 (here, the second cavity 106) by a predetermined action other than the inhalation action and the blow action. The predetermined action may be an action of blocking the aperture constituted by a tip end of the second electrode 212 with a hand finger cushion of a user, for example, and an action for increasing the inner pressure of the second cavity 106. In other words, the electrode member 210 has a configuration for increasing the inner pressure of the housing cavity 104 (here, the second cavity 106) by the predetermined action.

In the embodiment, the electrode member 210 is fitted into an inner side surface of the housing 100X. That is, the electrode member 210 is arranged not to protrude externally of an outer side surface of the housing 100X, in the shorter direction B. The electrode member 210 is preferably provided as a separate body of the housing 100X.

In the embodiment, the first cavity 105 and the second cavity 106 are partitioned by the sensor 20 not to communicate with each other within the housing 100X. The first cavity 105 may be considered as a cavity communicating from the ventilation aperture 101in and the mouthpiece aperture 100out to the sensor 20, and the second cavity 106 may be considered as a cavity communicating from the electrode member 210 to the sensor 20.

In the embodiment, the first configuration (the ventilation aperture 101in and the mouthpiece aperture 100out), the second configuration (the electrode member 210), and the sensor 20 are arranged in the order of the second configuration, the sensor 20, and the first configuration, from the non-mouthpiece end side toward the mouthpiece end side of the housing 100X.

The electrical unit 110 includes the battery 10, the sensor 20, a light-emitting element 40, and a control circuit 50.

The battery 10 is, for example, a lithium ion battery. The battery 10 accumulates the power necessary for the operation of the non-burning type flavor inhaler 100. For example, the battery 10 accumulates the power supplied to the sensor 20, the light-emitting element 40, and the control circuit 50. Moreover, the battery 10 accumulates the power supplied to an atomizer 80 (atomizer) described later.

The sensor 20 detects a change in the inner pressure of the housing cavity 104. In particular, the sensor 20 detects a differential pressure between the inner pressure of the first cavity 105 and the inner pressure of the second cavity 106.

Figure 3:
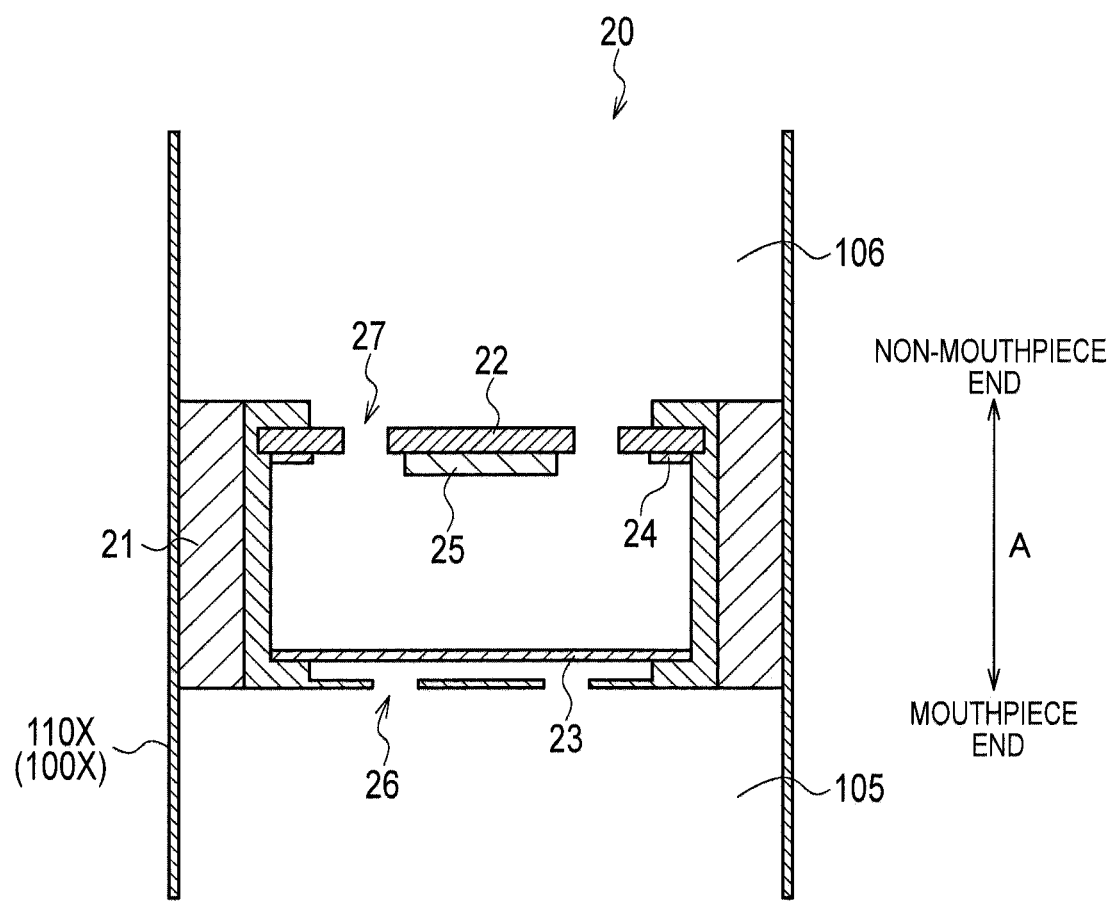
FIG. 3 is a diagram illustrating a sensor 20 according to the 20 embodiment.

For example, the sensor 20 is a sensor including a capacitor and outputs a value (for example, a voltage value) indicating the electric capacitance of the capacitor corresponding to the differential pressure between the inner pressure of the first cavity 105 and the inner pressure of the second cavity 106. As illustrated in FIG. 3, the sensor 20 includes a cover 21, a substrate 22, an electrode film 23, a fixed electrode 24, a control circuit 25, an aperture 26, and an aperture 27. There is no gap between the cover 21 and the housing 100X, and the first cavity 105 and the second cavity 106 are partitioned by the sensor 20 not to communicate with each other within the housing 100X. The substrate 22 is provided with the fixed electrode 24 and the control circuit 25. The electrode film 23 deforms depending on a change in the differential pressure between the inner pressure of the first cavity 105 and the inner pressure of the second cavity 106. The fixed electrode 24, together with the electrode film 23, forms a capacitor. The electric capacitance of the capacitor changes depending on the deformation of the electrode film 23. The control circuit 25 detects the electric capacitance that changes depending on the deformation of the electrode film 23. The aperture 26 communicates with the first cavity 105. Therefore, the inhalation action changes the inner pressure of the first cavity 105 and deforms the electrode film 23. The aperture 27 communicates with the second cavity 106. Therefore, the predetermined action changes the inner pressure of the second cavity 106 and deforms the electrode film 23.

Specifically, for example, if the inhalation action is performed, the inner pressure of the first cavity 105 is reduced whereas the inner pressure of the second cavity 106 does not substantially change and is almost equal to the atmospheric pressure, and thus, the sensor 20 substantially detects the pressure change in the first cavity 105. In addition, for example, if the blow action is performed, the inner pressure of the first cavity 105 is increased whereas the inner pressure of the second cavity 106 does not substantially change and is almost equal to the atmospheric pressure, and thus, the sensor 20 substantially detects the pressure change in the first cavity 105. In addition, for example, if the predetermined action is performed, the inner pressure of the second cavity 106 is increased whereas the inner pressure of the first cavity 105 does not substantially change and is almost equal to the atmospheric pressure, and thus, the sensor 20 substantially detects the pressure change in the second cavity 106.

Returning to FIG. 1, the light-emitting element 40 notifies a state of the non-burning type flavor inhaler 100 by a light-emitting manner, that is, a color of light emission, lighting on/lighting off, a pattern during lighting on, etc. The state of the non-burning type flavor inhaler 100 may include a state such as power source on or power source off, and a state such as an inhaling state or a non-inhaling state, for example. In such a case, the light-emitting element 40 is preferably provided to be closer to the mouthpiece end side of the housing 100X than the electrode member 210. Further, the light-emitting element 40 is preferably provided to be closer to the mouthpiece end side of the housing 100X than the second cavity 106. According to such a constitution, the light-emitting element 40 may be easily recognized during the inhalation action/blow action and the predetermined action. Alternatively, the state of the non-burning type flavor inhaler 100 may include a value managed by a controller 51 described later (for example, the cumulative number of times of puff actions, the cumulative number of times of puff actions in one puff action series, the cumulative number of times of puff action series, a remaining amount of the battery 10, a remaining amount of an aerosol source, and the like).

The control circuit 50 controls an operation of the non-burning type flavor inhaler 100. It is noted that the control circuit 50 will be described in detail later (see FIG. 4).

As illustrated in FIG. 2, the atomizing unit 120 includes a reservoir 60, a liquid holding member 70, an atomizer 80, and a destruction unit 90. The atomizing unit 120 includes a capsule unit 130 and a mouthpiece unit 140. Here, the atomizing unit 120 includes the aperture 120in through which an atmospheric air is absorbed internally, an air flow path 122 communicating with the electrical unit 110 (sensor 20) via the male connector 121, and a ceramic 123 arranged in a cylindrical shape. The atomizing unit 120 includes a tubular atomizing housing 120X forming an external shape of the atomizing unit 120. A space enclosed by the ceramic 123 forms an air flow path. That is, the space enclosed by the ceramic 123 and the above-described air flow path 122 form a part of the first cavity 105. The ceramic 123, for example, includes alumina as the main constituent.

In the reservoir 60, an aerosol source is retained. The reservoir 60 has a porous body constituted of a material such as a resin web. The reservoir 60 may well be arranged at a position allowing the aerosol source to be supplied to the liquid holding member 70, and at least contacts a part of the liquid holding member 70.

It is noted that in the embodiment, the above-described ceramic 123 is arranged on the inner side of the reservoir 60, and the volatilization of the aerosol source held by the reservoir 60 is thus controlled.

The liquid holding member 70 holds the aerosol source supplied from the reservoir 60. For example, the liquid holding member 70 is a wick constituted by a glass fiber.

The atomizer 80 heats the aerosol source without burning. That is, the atomizer 80 atomizes, without burning, the aerosol source held by the liquid holding member 70. For example, the atomizer 80 is a resistance heating element generating heat by a power source output supplied to the atomizer 80. The atomizer 80 may be constituted by a wire wound around the liquid holding member 70.

In the embodiment, a heating type component configured to atomize the aerosol source by heating is illustrated as the atomizer 80. However, as long as the atomizer has a function of atomizing the aerosol source, the atomizer may be an ultrasonic wave type component configured to atomize the aerosol source by an ultrasonic wave.

The breaker 90 is a member for breaking a part of predetermined film 133 in the state that the capsule unit 130 is mounted. In the embodiment, the breaker 90 is held by a partition member 126 for partitioning the atomizing unit 120 and the capsule unit 130. The partition member 126 is made of Polyacetal resin. The breaker 90 is a hollow cylindrical needle extending along a longer direction A, for example. By piercing a tip of the hollow needle into a predetermined film 133, a part of the predetermined film 133 is broken. Further, an inner space of the hollow needle forms an airflow path that communicates pneumatically the atomizing unit 120 with the capsule unit 130. It is preferable that a mesh having a roughness of not passing a material composing the tobacco source 131 is provided inside the hollow needle. The roughness of the mesh is 80 meshes or more and 200 meshes or less, for example.

In such a case, the insertion depth of the hollow needle into the capsule unit 130 is preferably 1.0 mm or more and 5.0 mm or less, more preferably, 2.0 mm or more and 3.0 mm or less. At this insertion depth, the parts except a desired portion are not broken, suppressing detachment of the tobacco source 131 filled in the space which is partitioned by the predetermined film 133 and the filter 132. Furthermore, since the detachment of the hollow needle from the space is suppressed, a proper airflow path to the filter 132 from the hollow needle can be preferably maintained.

In a vertical section with respect to the longer direction A, a sectional area of a vertical needle is preferably 2.0 mm$^2$ or more and 3.0 mm$^2$ or less. Thus, the tobacco source 131 is prevented from falling off the capsule unit 130 when the hollow needle is removed.

The tip of the hollow needle preferable has an inclination of 30° or more and 45° or less with respect to the vertical direction to the longer direction A.

However, the embodiment is not limited to this. The breaker 90 may be a part adjacent to the predetermined film 133 in a state that the capsule unit 130 is mounted. A part of the predetermined film 133 may be broken by a pressure applied to such a part by a user.

The capsule unit 130 is configured to be attachable/detachable to/from the main body unit. The capsule unit 130 comprises a tobacco source 131, a filter 132, and a predetermined film 133. The tobacco source 131 is filled in a space partitioned by the predetermined film 133 and the filter 132. The main body unit is a unit that is composed of parts other except the capsule unit 130. For example, the main body unit includes the electrical unit 110, the reservoir 60, the liquid holding member 70 and the atomizer 80.

The tobacco source 131 is provided on the inhalation end side than the reservoir 60 holding the aerosol source, and generates flavor inhaled by a user together with aerosol generated by the aerosol source. It is noted that the tobacco source 131 is composed of a solid substance so as not to flow out of the space partitioned by the predetermined film 133 and the filter 132. As a tobacco source 131, it is possible to use shredded tobacco, a molded body of granulated tobacco material, and a molded body formed into a sheet tobacco material. The tobacco source 131 may be given flavors such as menthol.

When the tobacco source 131 is composed of tobacco material, as the tobacco material is apart from the atomizer 80, it is possible to inhale the flavor without heating the tobacco material. In other words, it is noted that inhalation of unwanted substance generated by heating the tobacco material is suppressed.

In the embodiment, the amount of the tobacco source 131 filled in the space partitioned by the filter 132 and the predetermined film 133 is preferably 0.15 g/cc or more and 1.00 g/cc or less. The volume occupancy of the tobacco source 131 in the space partitioned by the filter 132 and the predetermined film 133 is preferably 50% or more and 100% or less. The volume of the space partitioned by the filter 132 and the predetermined film 133 is preferably 0.6 ml or more and 1.5 ml or less. In such conditions, the tobacco source 131 can be contained to the extent enough to enable a user to taste flavor while maintaining an appropriate size of the capsule unit 130.

In the state where a part of the predetermined film 133 is broken by the breaker 90 and where the atomizing unit 120 communicates with the capsule unit 130, when air is inhaled from a tip portion (non-broken portion) of the capsule unit 130 to a distal end of the filter 132 at a flow rate of 1050 cc/min, an airflow resistance (pressure loss) of the capsule unit 130 is preferably 10 mmAq or more and 100 mmAq or less, as a whole, more preferably, 20 mmAq or more and 90 mmAq or less. By setting the airflow resistance of the tobacco source 131 to the above preferable range, aerosol is prevented from being overly filtered by the tobacco source 131, and thus flavor can be efficiently supplied to a user. Incidentally, 1 mmAq corresponds to 9.80665 Pa, and the airflow resistance can be expressed by Pa.

The filter 132 is adjacent to the inhalation end side with respect to the tobacco source 131, and is composed of a permeable substance. The filter 132 is preferably an acetate filter, for example. The filter 132 preferably has roughness of a degree not to pass through a material constituting the tobacco source 131.

An airflow resistance of the filter 132 is preferably 5 mmAq or more and 20 mmAq or less. Accordingly, it is possible to efficiently pass through aerosol while efficiently absorbing a vapor component generated by the tobacco source 131, and thus proper flavor can be supplied to a user. Further, it is possible to give a user an appropriate feeling of air resistance.

A ratio (mass ratio) between the mass of the tobacco source 131 and the mass of the filter 132 is preferably in a range of 3:1 to 20:1, more preferably, in a range of 4:1 to 6:1.

The predetermined film 133 is formed integrally with the filter 132, and is composed of impermeable material. The predetermined film 133 covers a part of the outer surface of the tobacco source 131 except a portion adjacent to the filter 132. The predetermined film 133 includes at least one compound selected from a group consisting of gelatin, polypropylene and polyethylene terephthalate. Gelatin, polypropylene, polyethylene and polyethylene terephthalate are not permeable, and suitable for forming a thin film. Gelatin, polypropylene, polyethylene and polyethylene terephthalate provide a sufficient resistance to moisture contained in the tobacco source 131. Polypropylene, polyethylene and polyethylene terephthalate are especially excellent in a water resistance. Further, gelatin, polypropylene and polyethylene have a base resistance, and are thus hardly degraded by a basic component, even when the tobacco source 131 has a basic component.

A thickness of the predetermined film 133 is preferably 0.1 μm or more and 0.3 μm or less. Accordingly, it is possible to easily break a part of the predetermined film 133 while maintaining a function of protecting the tobacco source 131 by the predetermined film 133.

As described above, although the predetermined film 133 is formed integrally with the filter 132, the predetermined film 133 is bonded to the filter 132 by paste or the like. Or, by setting the outer shape of the predetermined film 133 smaller than that of the filter 132 in the vertical direction with respect to the longer direction A, the filter 132 may be stuffed into the predetermined film 133 and may be fitted into the predetermined film 133 by a restoring force of the filter 132. Alternatively, the filter 132 may be provided with an engagement part for engaging the predetermined film 133.

A shape of the predetermined film 133 is not particularly limited, but preferably has a concave shape in the vertical cross-section with respect to the longer direction A. In such a case, after filling the tobacco source 131 inside the predetermined film 133 having the concave shape, an opening of the predetermined film 133 filled with the tobacco source 131 is closed by the filter 132.

When the predetermined film 133 has the concave shape in the vertical cross-section with respect to the longer direction A, a maximum sectional area (i.e., a sectional area of an opening in which the filter 132 is fitted) of the sectional area of the space surrounded by the predetermined film 133, is preferably 25 $mm^2$ or more and 80 $mm^2$ or less, more preferably, 25 $mm^2$ or more and 55 $mm^2$ or less. In such a case, in the vertical cross-section with respect to the longer direction A, a sectional area of the filter 132 is preferably 25 $mm^2$ or more and 55 $mm^2$ or less. A thickness of the filter 132 in the longer direction A is preferably 3.0 mm or more and 7.0 mm or less.

The mouthpiece unit 140 has an mouthpiece hole 120out. The mouthpiece hole 120out is an opening to expose the filter 132. A user inhales flavor together with aerosol by inhaling aerosol through the mouthpiece hole 120out.

In the embodiment, the mouthpiece unit 140 is configured to be attachable/detachable to/from the atomizing housing 120X of the atomizing unit 120. For example, the mouthpiece unit 140 has a cup shape configured to be fitted to an inner surface of the atomizing housing 120X. However, the embodiment is not limited to this. The mouthpiece unit 140 may be attached rotatably to the atomizing housing 120X with a hinge or the like.

In the embodiment, the mouthpiece unit 140 is provided separately from the capsule unit 130. In other words, the mouthpiece unit 140 constitutes a part of the main body unit. However, the embodiment is not limited to this. The mouthpiece unit 140 may be provided integrally with the capsule unit 130. In such a case, it is noted that the mouthpiece unit 140 constitutes a part of the capsule unit 130.

Control Circuit

Figure 4:
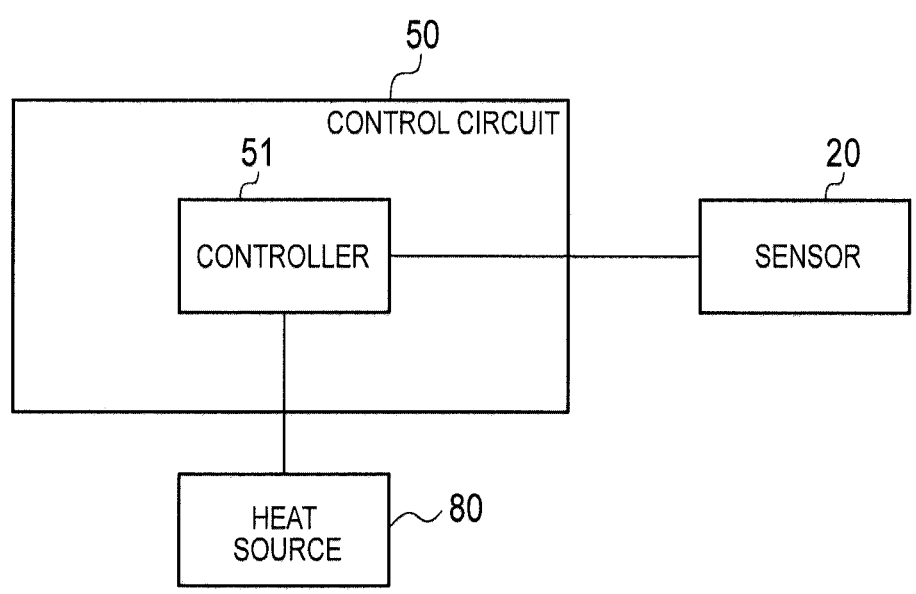
FIG. 4 is a block diagram illustrating a control circuit 50 according to the embodiment.

A control circuit according to the embodiment will be described, below. FIG. 4 is a block diagram illustrating the control circuit 50 according to the embodiment.

As illustrated in FIG. 4, the control circuit 50 is connected to the sensor 20, and includes a controller 51 configured to control at least the atomizer. The controller 51 performs atomizing control of the atomizer for starting or terminating atomization of the aerosol source, based on at least the inhalation action (output value of the sensor 20). The controller 51 performs predetermined control different from the atomizing control of the atomizer, based on the predetermined action (output value of the sensor 20).

Here, the output value of the sensor 20 is compared with a first threshold value to determine whether or not to perform the atomizing control of the atomizer and a second threshold value to determine the predetermined control different from the atomizing control of the atomizer. The first threshold value is larger than the second threshold value. It is noted that a threshold value (first threshold value) to determine the start of the atomization of the aerosol source (start of a power source output) may be different from a threshold value (first threshold value) to determine the termination of the atomization of the aerosol source (stopping of the power source output).

Specifically, if the inner pressure of the first cavity 105 is decreased, by the inhalation action, than that of the second cavity 106 and the output value of the sensor 20 configured to detect the change in inner pressure inside the housing cavity 104 exceeds the first threshold value, the controller 51 starts the power source output to the atomizer 80. On the other hand, if the inner pressure of the first cavity 105 is decreased than that of the second cavity 106 and the output value of the sensor 20 configured to detect the change in inner pressure inside the housing cavity 104 falls below the first threshold value, the controller 51 stops the power source output to the atomizer 80. Further, if the inner pressure of the second cavity 106 is increased, by the predetermined action, than that of the first cavity 105 and the output value of the sensor 20 configured to detect the pressure change inside the housing cavity 104 does not exceed the first threshold value but exceeds the second threshold value, the controller 51 performs the predetermined control different from the atomizing control of the atomizer.

Therefore, it should be noted that the above-described electrode member 210 may be considered to have a configuration for changing the inner pressure of the housing cavity 104 (second cavity 106) so that the output value of the sensor 20 does not exceed the first threshold value and the output value of the sensor 20 exceeds the second threshold value.

It is noted that the predetermined control may be control for determining whether or not the user is an authorized user, and may be control for starting or terminating a puff action series. The puff action series is a series of actions in which the inhalation action is repeated a predetermined number of times. Alternatively, in a case where a plurality of operation modes are provided as an operation mode of the non-burning type flavor inhaler 100, the predetermined control may be control for switching the operation modes. For example, the switching of the operation modes is a switching between a sleep mode (power save mode) in which the atomizing control of the atomizer for starting or terminating atomization of the aerosol source is not permitted based on the inhalation action (output value of the sensor 20) and energization to at least the sensor 20 is performed; and a ready mode in which the atomizing control of the atomizer for starting or terminating atomization of the aerosol source is permitted based on the inhalation action (output value of the sensor 20) and the energization to at least the sensor 20 is performed. Alternatively, the switching of the operation modes is a switching of a magnitude of the power source output (an absolute value or a duty ratio of the power source output) to the atomizer 80. Alternatively, the switching of the operation modes is a switching of whether or not to permit communication using a communication module, in a case where the non-burning type flavor inhaler 100 includes a communication module. Alternatively, the predetermined control may be reset control of a value counted in the controller 51 (for example, the cumulative number of times of puff actions, the cumulative number of times of puff actions in one puff action series, the cumulative number of times of puff action series, and the like). Alternatively, the predetermined control may be control for notifying a value managed by the controller 51 (for example, the cumulative number of times of puff actions, the cumulative number of times of puff actions in one puff action series, the cumulative number of times of puff action series, the remaining amount of the battery 10, the remaining amount of the aerosol source, whether or not the communication using the communication module is in an enabled state, and the like) by a light-emitting manner of the light-emitting element 40.

Here, at least one of the first threshold value and the second threshold value may be a value compared with an absolute value of the output value of the sensor 20. Alternatively, at least one of the first threshold value and the second threshold value may be a value compared with a gradient constituted by two or more output values of the sensors 20.

The controller 51 is connected to the battery 10, and controls the power source output (here, the power amount) to the atomizer 80 (atomizer) from the battery 10. It is noted that the power amount is the result of multiplication of time and power (voltage or current), and is a value that is controlled by time and power. For example, the controller 51 controls the voltage applied to the atomizer 80 from the battery 10 by controlling a DC-DC converter or the like arranged together with the battery 10. The controller 51 may control the absolute value of the power source output to the atomizer 80 and may control the duty ratio of the power source output to the atomizer 80.

It is noted that the controller 51 may perform the predetermined control, based on the blow action, and may not need to perform the predetermined control (may not need to perform any control even if detecting the blow action). Alternatively, the sensor 20 may be constituted to be capable of detecting the inhalation action only. The predetermined control based on the blow action can be appropriately selected from control listed as predetermined control, based on the above-described predetermined action, different from the atomizing control of the atomizer. It is noted that if the predetermined control is performed based on the blow action, the predetermined control based on the blow action is preferably different from the predetermined control based on the predetermined action.

Operation and Effect

In the embodiment, the non-burning type flavor inhaler 100 includes the first configuration for changing the inner pressure of the first cavity 105 by the inhalation action or the blow action; and the second configuration for changing the inner pressure of the second cavity 106 by the predetermined action other than the inhalation action and the blow action, in which the sensor 20 detects the change in the inner pressure of the housing cavity 104. According to such a constitution, as a member configured to detect a trigger for performing predetermined control different from the atomizing control, the sensor 20 used for the atomizing control is used, and thus, a wider range of usage of the sensor 20 used for the atomizing control is realized. Further, the trigger for performing a plurality of controls is detected by one sensor 20, and thus, it is also possible to decrease the number of components.

In the embodiment, the electrode member 210 (aperture 214) is provided on the end surface of the non-mouthpiece end of the housing 100X. According to such a constitution, it is possible to suppress the predetermined action for increasing the inner pressure of the second cavity 106 from being erroneously performed along with the inhalation action.

In the embodiment, the first configuration (the ventilation aperture 101in and the mouthpiece aperture 100out), the second configuration (the electrode member 210), and the sensor 20 are arranged in the order of the second configuration, the sensor 20, and the first configuration, from the non-mouthpiece end side toward the mouthpiece end side of the housing 100X. Further, the first cavity 105 is provided at the mouthpiece end side relative to the sensor 20, and the second cavity 106 is provided at a non-mouthpiece end side relative to the sensor 20. According to such a constitution, an magnitude relation of the inner pressures (the inner pressure of the first cavity 105<the inner pressure of the second cavity 106) occurring due to the predetermined action for increasing the inner pressure of the second cavity 106 is the same as that of the inner pressure occurring due to the inhalation action, whereas the magnitude relation of the inner pressures occurring due to the blow action is the inner pressure of the first cavity 105>the inner pressure of the second cavity 106, and thus, it is easy to distinguish between the predetermined action and the blow action.

In the embodiment, the first cavity 105 and the second cavity 106 are partitioned by the sensor 20 not to communicate with each other within the housing 100X. According to such a constitution, it is possible to easily increase the inner pressure of the second cavity 106 by the second configuration, and besides, it is possible to suppress the change in inner pressure of the first cavity 105 by the predetermined action, resulting in a higher detection accuracy of the predetermined action.

In the embodiment, the electrode member 210 is arranged not to protrude externally of the outer side surface of the housing 100X, in the shorter direction B. Therefore, even if the electrode member 210 is provided which is configured to change the inner pressure of the second cavity 106 by the predetermined action, an increase in size of the non-burning type flavor inhaler 100 in the shorter direction B can be suppressed.

First Modification

A first modification of the embodiment will be described, below. A difference from the embodiment will be mainly described, below.

In the first modification, as the second configuration for changing the inner pressure of the second cavity 106 by the predetermined action, an endcap 220 is provided instead of the electrode member 210, as illustrated in FIG. 5(A) or FIG. 5(B). The endcap 220 is provided at the non-mouthpiece end of the housing 100X (electrical housing 110X), and covers the aperture of the second cavity 106.

For example, as illustrated in FIG. 5(A), the endcap 220 has a shape depressed inwardly into the electrical housing 110X, in the longer direction A, and includes an aperture 221 communicating from the second cavity 106 to the aerospace outside the electrical housing 110X. Alternatively, as illustrated in FIG. 5(B), the endcap 220 may not need to have a shape depressed inwardly into the electrical housing 110X. In such a case, the aperture 221 preferably has a size allowing a hand finger cushion of the user to enter in the electrical housing 110X. It is noted that the aperture 221 is provided on the end surface of the non-mouthpiece end of the electrical housing 110X.

According to these constitutions, it is possible to increase the inner pressure of the second cavity 106 by an action (predetermined action) of blocking the aperture 221 with a hand finger cushion or the like.

Second Modification

A second modification of the embodiment will be described, below. A difference from the first modification will be mainly described, below.

In the second modification, as illustrated in FIG. 6(A) to FIG. 6(C), similarly to the first modification, the endcap 220 is provided at the non-mouthpiece end of the housing 100X (electrical housing 110X). In the second modification, at least a part of the endcap 220 is constituted of an elastic member. For example, as illustrated in FIG. 6(A), the endcap 220 may completely cover the aperture of the second cavity 106. Alternatively, as illustrated in FIG. 6(B), the endcap 220 may include one or more apertures 221 communicating from the second cavity 106 to the aerospace outside the electrical housing 110X. The aperture 221 is provided on the end surface of the non-mouthpiece end of the electrical housing 110X. Alternatively, as illustrated in FIG. 6(C), the electrical housing 110X may include an aperture 222 communicating from the second cavity 106 to the aerospace outside the electrical housing 110X. The aperture 222 is provided on a surface (here, a side surface) facing a different direction from the end surface of the non-mouthpiece end in the electrical housing 110X, for example. In FIG. 6(C), the second configuration includes a part of the housing forming the endcap 220 and the aperture 222.

At least a part of the endcap 220 is constituted by the elastic member, and thus, it is possible to increase the inner pressure of the second cavity 106 by an action (predetermined action) for depressing the endcap 220 toward the inside the electrical housing 110X. It should be noted that in a case illustrated in FIG. 6(C), unless the endcap 220 is depressed while the aperture 222 is blocked, the inner pressure of the second cavity 106 is not increased.

Third Modification

A third modification of the embodiment will be described, below. A difference from the embodiment will be mainly described, below.

Figure 7:
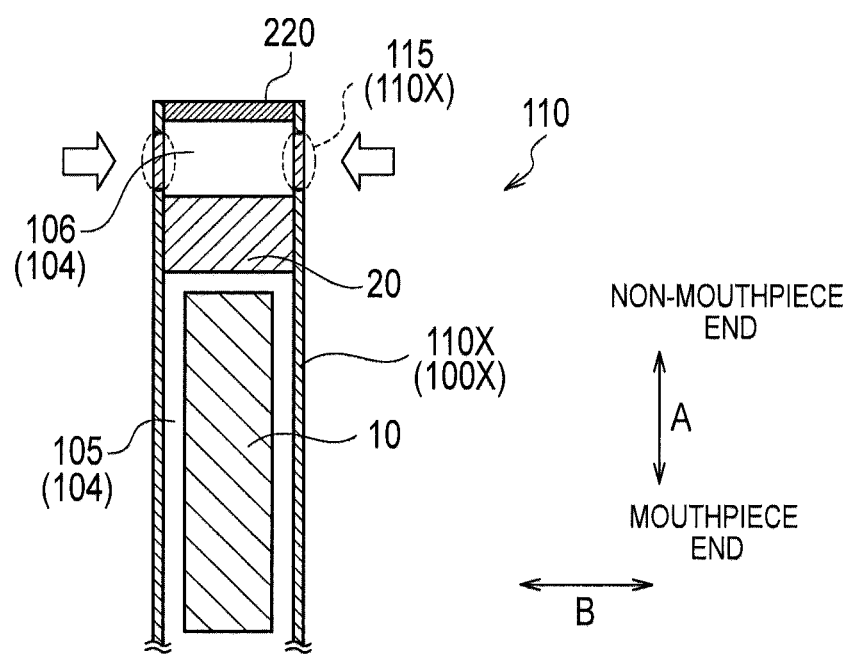
FIG. 7 is a diagram illustrating the electrical unit 110 according to a third modification.

In the third modification, as illustrated in FIG. 7, the housing 100X (electrical housing 110X) includes an elastic portion 115 constituted of an elastic member. The elastic portion 115 constitutes a part of a partition wall partitioning the second cavity 106. The elastic portion 115 constitutes a part of the second configuration for changing the inner pressure of the second cavity 106 by the predetermined action. It is noted that the aperture of the second cavity 106 is covered with the endcap 220 as in the first modification or the like. Similarly to the elastic portion 115, the endcap 220 also constitutes a part of the second configuration.

Apart of the partition wall partitioning the second cavity 106 is constituted of the elastic portion 115, and thus, it is possible to increase the inner pressure of the second cavity 106 by the action (predetermined action) for depressing the elastic portion 115 toward the inside the electrical housing 110X.

Fourth Modification

A fourth modification of the embodiment will be described, below. A difference from the embodiment will be mainly described, below.

In the fourth modification, as the second configuration for changing the inner pressure of the second cavity 106 by the predetermined action, a slide member 230 is provided instead of the electrode member 210, as illustrated in FIG. 8(A) or FIG. 8(B). The slide member 230 is provided at the non-mouthpiece end of the housing 100X (electrical housing 110X), and covers the aperture of the second cavity 106. The slide member 230 is constituted to be slidable along the longer direction A to change the volume of the second cavity 106. For example, as illustrated in FIG. 8(A), the slide member 230 is constituted to be slidable along an outer side surface of the electrical housing 110X. Alternatively, as illustrated in FIG. 8(B), the slide member 230 may be constituted to be slidable along an inner side surface of the electrical housing 110X. In a case illustrated in FIG. 8(B), the slide member 230 may include an elastic member 231 (spring or the like) so that the endcap 220 is automatically returned to the original position by the elastic member 231 after the slide member 230 is slid.

According to these constitutions, it is possible to increase the inner pressure of the second cavity 106 by the slide (predetermined action) of the slide member 230.

Fifth Modification

A fifth modification of the embodiment will be described, below. A difference from the embodiment will be mainly described, below.

In the fifth modification, as the second configuration for changing the inner pressure of the second cavity 106 by the predetermined action, a movable member 240 is provided instead of the electrode member 210, as illustrated in FIG. 9. The movable member 240 is constituted to be movable within the housing cavity 104 (here, the second cavity 106). The movable member 240 is preferably held by the endcap 220 configured to cover the aperture of the second cavity 106. The inner pressure of the second cavity 106 is changed by the movement of the movable member 240.

The movable member 240 is provided in the second cavity 106, and thus, if the movable member 240 is moved in the second cavity 106 by an action (predetermined action) for swinging the non-burning type flavor inhaler 100, for example, it is possible to increase the inner pressure of the second cavity 106.

Sixth Modification

A sixth modification of the embodiment will be described, below. A difference from the embodiment and the first modification will be mainly described, below.

As described above, in the first modification, as the second configuration for changing the inner pressure of the second cavity 106 by the predetermined action, the endcap 220 is provided which is configured to cover the aperture of the second cavity 106, as illustrated in FIG. 5(A) or FIG. 5(B). The endcap 220 includes the aperture 221 communicating from the second cavity 106 to the aerospace outside the electrical housing 110X.

Figure 10A:
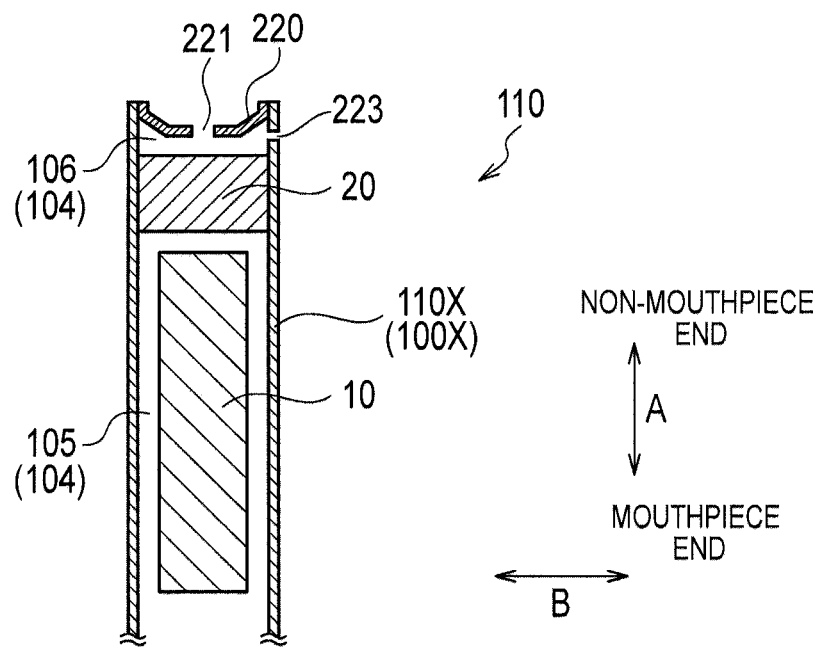
FIGS. 10A and 10B are diagrams illustrating the electrical unit 110 according to a sixth modification.
Figure 10B:
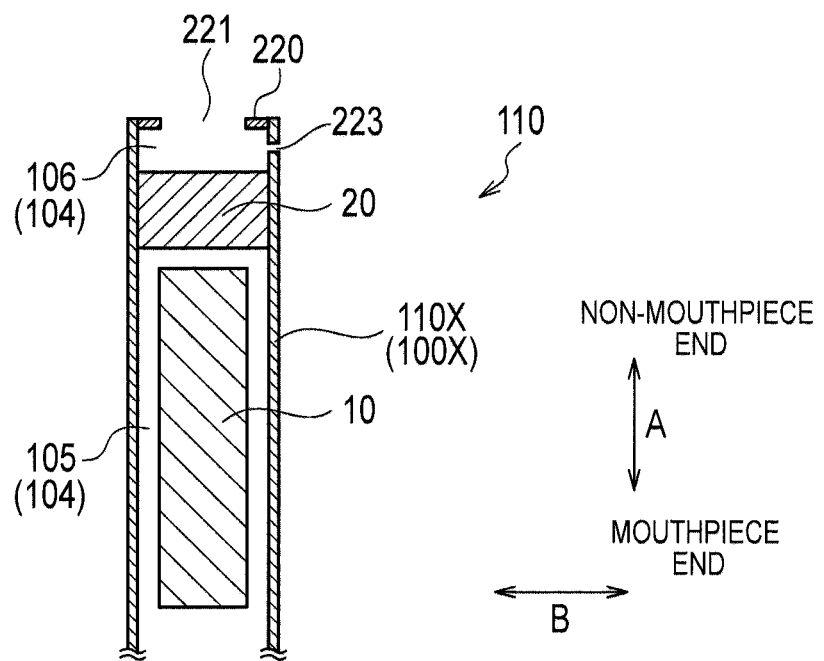

In contrast, in the sixth modification, as illustrated in FIG. 10(A) and FIG. 10(B), other than the aperture 221 provided in the endcap 220, an aperture 223 is provided which communicates from the second cavity 106 to the aerospace outside the electrical housing 110X. The aperture 223 is provided in the electrical housing 110X, for example. In such a case, the second configuration includes a part of the housing forming the endcap 220 and the aperture 223. It should be noted that in a case illustrated in FIG. 10(A) and FIG. 10(B), unless the aperture 221 is blocked with a hand finger cushion or the like while the aperture 223 is blocked, the inner pressure of the second cavity 106 is not increased.

That is, in the sixth modification, the aperture 221 and the aperture 223 are provided as the aperture included in the second configuration, and the aperture 221 and the aperture 223 are provided on surfaces facing directions different from each other in the electrical housing 110X. For example, the aperture 221 is provided on the end surface of the non-mouthpiece end of the electrical housing 110X, and the aperture 223 is provided on a side surface of the electrical housing 110X.

In the present invention, the aperture 223 may be a single aperture, and may include a plurality of apertures. Here, the size of the aperture 223 preferably includes a size not allowing a hand finger cushion of the user to enter in the electrical housing 110X. For example, a minimum width of the aperture 223 passing through the center of gravity of the aperture 223 is preferably 5 mm or less, and preferably 3 mm or less. Alternatively, the area of the aperture 223 is preferably 20 $mm^2$ or less, and more preferably 7 $mm^2$ or less. If the aperture 223 is a circular aperture, the diameter of the aperture 223 is preferably 5 mm or less, and more preferably 3 mm or less. Meanwhile, if only the aperture 221 is blocked while the aperture 223 is not blocked, the aperture 223 preferably has air permeability not allowing the output value of the sensor 20 to exceed the second threshold value. If a plurality of apertures are provided, each aperture more preferably satisfies the above-described minimum width and area, and if the plurality of apertures are circular apertures, each aperture more preferably satisfies the above-described diameter. In a case illustrated in FIG. 10(A), the relationship of sizes between the aperture 221 and the aperture 223 is not concerned; however, in a case illustrated in FIG. 10(B), the aperture 221 is preferably larger than the aperture 223. The aperture 223 provided on the side surface of the electrical housing 110X is preferably provided between the end surface of the non-mouthpiece end of the electrical housing 110X and the sensor 20.

As above, in the sixth modification, the second configuration includes two or more apertures communicating from the second cavity 106 to the aerospace outside the housing 100X. Therefore, unless the two or more apertures are blocked with a hand finger cushion or the like, the inner pressure of the second cavity 106 is not increased. As a result, it is possible to effectively suppress an erroneous action in which the predetermined control is performed unintentionally.

It is noted that in a case where the second configuration includes a plurality of apertures, the apertures 223 blocked first may be provided on the end surface of the non-mouthpiece end of the housing, and the aperture 221 blocked to increase the inner pressure of the housing cavity may be provided on the side surface of the non-mouthpiece end of the housing.

Further, as described in the embodiment, in a case where the electrode member 210, rather than the endcap 220, is provided in the non-burning type flavor inhaler 100, an aperture communicating from the second cavity 106 to the aerospace outside the electrical housing 110X may be provided in addition to the aperture 214 provided in the electrode member 210.

Other Embodiments

The present invention is described through the above-described embodiments, but it must not be understood that this invention is limited by the statements and the drawings constituting a part of this disclosure. From this disclosure, various alternative embodiments, examples, and operational technologies will become apparent to those skilled in the art.

In the embodiment, the first cavity 105 and the second cavity 106 are partitioned by the sensor 20. However, the embodiment is not limited thereto. Specifically, the first cavity 105 and the second cavity 106 may not need to be partitioned yet the first cavity 105 and the second cavity 106 may be connected. Alternatively, the second cavity 106 may constitute a part of the first cavity 105. In such a case, the above-described ventilation aperture 101in may not need to be provided, and only one aperture may be provided on the end surface of the non-mouthpiece end of the housing 110X. In such a case, the controller 51 performs the atomizing control of the atomizer (control of the power source output to the atomizer 80), based on the inhalation action of the user. In addition, the controller 51 performs the predetermined control different from the atomizing control of the atomizer, based on the predetermined action different from the inhalation action and the blow action of the user. The predetermined action different from the inhalation action and the blow action may be an action for increasing the inner pressure of the housing cavity 104, and is, for example, an action of blocking one aperture with a hand finger cushion of the user.

In the embodiment, the electrode member 210 is provided on the end surface of the non-mouthpiece end of the housing 100X; however, the embodiment is not limited thereto. The electrode member 210 may be provided on the side surface of the non-mouthpiece end side of the housing 100X.

In the embodiment, the electrode member 210 is provided as a member configured to charge the battery 10. However, the embodiment is not limited thereto. The member configured to charge the battery 10 may be the female connector 111 provided in the electrical unit 110. That is, the female connector 111 may be connected to the battery 10, and may supply the power to the battery 10 by connecting an external power source and the battery 10.

In the embodiment, the cover 21 of the sensor 20 partitions the first cavity 105 and the second cavity 106 not to communicate with each other within the housing 100X. However, the embodiment is not limited thereto. The cover 21 may include an aperture allowing the first cavity 105 to communicate with the second cavity 106. Alternatively, it may be possible that the aperture is not provided in the cover 21, but the electrode film 23 includes an aperture allowing the first cavity 105 to communicate with the second cavity 106.

In the embodiment, the tobacco source 131 is illustrated as the flavor source. However, the embodiment is not limited thereto. The flavor source may not necessarily include a tobacco raw material. In addition, it may be possible that the non-burning type flavor inhaler 100 does not include a flavor source, and an inhaling flavor component is added to the aerosol source.

In the embodiment, a case is illustrated in which the non-burning type flavor inhaler 100 includes the capsule unit 130. However, the embodiment is not limited thereto. For example, the non-burning type flavor inhaler 100 may include a cartridge containing the flavor source.

In the embodiment, a case is described in which the sensor 20 is a sensor including a capacitor. However, the type of sensor 20 is not limited thereto. The sensor 20 may just be required to detect the change in inner pressure of the housing cavity 104. Preferably, the sensor 20 may just be required to detect the differential pressure between the inner pressure of the first cavity 105 and the inner pressure of the second cavity 106.

INDUSTRIAL APPLICABILITY

According to the present invention, it is possible to realize a wider range of usage of a sensor used for atomizing control.

The invention claimed is:

1. A non-burning type flavor inhaler comprising:
a housing having a housing cavity;
an atomizer configured to atomize an aerosol source without burning;
a sensor configured to detect a change in inner pressure of the housing cavity;
a controller configured to control at least the atomizer;
a first configuration for changing the inner pressure of the housing cavity by an inhalation action or a blow action; and
a second configuration for changing the inner pressure of the housing cavity by a predetermined action other than the inhalation action and the blow action, wherein
the first configuration includes a mouthpiece aperture provided on a mouthpiece end of the housing,
the controller is configured to perform an atomizing control for starting or terminating atomization of the aerosol source, based on at least the change of the inner pressure of the housing cavity caused by the inhalation action, and
the controller is configured to perform a predetermined control other than the atomizing control, based on the change of the inner pressure of the housing cavity caused by the predetermined action.

2. The non-burning type flavor inhaler according to claim 1, wherein
the first configuration includes an aperture allowing for communication between the housing cavity and an aerospace outside the housing, and
the aperture included in the first configuration communicates with the mouthpiece aperture.

3. The non-burning type flavor inhaler according to claim 1, wherein
the second configuration has a configuration for increasing the inner pressure of the housing cavity by the predetermined action.

4. The non-burning type flavor inhaler according to claim 1, wherein
the first configuration, the second configuration, and the sensor are arranged in order of the second configuration, the sensor, and the first configuration, from a non-mouthpiece end side toward a mouthpiece end side of the housing.

5. The non-burning type flavor inhaler according to claim 1, wherein
the second configuration is provided at a non-mouthpiece end of the housing.

6. The non-burning type flavor inhaler according to claim 1, wherein
the housing cavity includes a first cavity communicating from the first configuration to the sensor and a second cavity communicating from the second configuration to the sensor, and the first cavity and the second cavity are partitioned not to communicate with each other within the housing.

7. The non-burning type flavor inhaler according to claim 1, wherein
the controller is configured to compare an output value of the sensor with a first threshold value to determine whether or not to perform the atomizing control of the atomizer and is configured to compare the output value of the sensor with a second threshold value to determine the predetermined control other than the atomizing control of the atomizer, and
the first threshold value is larger than the second threshold value.

8. The non-burning type flavor inhaler according to claim 7, wherein
the second configuration has a configuration for changing the inner pressure of the housing cavity so that the output value of the sensor does not exceed the first threshold value and the output value of the sensor exceeds the second threshold value.

9. The non-burning type flavor inhaler according to claim 1, wherein
the second configuration includes an aperture communicating from the housing cavity to the aerospace outside the housing.

10. The non-burning type flavor inhaler according to claim 9, wherein
the aperture included in the second configuration is provided on an end surface of a non-mouthpiece end of the housing.

11. The non-burning type flavor inhaler according to claim 9, wherein
a first aperture and a second aperture are arranged as the aperture included in the second configuration, and
the first aperture and the second aperture are provided on surfaces facing directions different from each other in the housing.

12. The non-burning type flavor inhaler according to claim 9, wherein
a first aperture and a second aperture are provided as the aperture included in the second configuration,
the first aperture is provided on an end surface of a non-mouthpiece end of the housing, and
the second aperture is provided on a side surface of the housing.

13. The non-burning type flavor inhaler according to claim 1, wherein
the housing has a longer direction and a shorter direction perpendicular to the longer direction, and the second configuration is arranged not to protrude externally of an outer side surface of the housing in the shorter direction.

14. The non-burning type flavor inhaler according to claim 1, wherein
the second configuration is provided as a separate body from the housing.

15. The non-burning type flavor inhaler according to claim 1, wherein
a non-mouthpiece end of the housing is provided with an electrode member configured to charge a power source for supplying at least power to the atomizer, and
the second configuration includes the electrode member.

16. The non-burning type flavor inhaler according to claim 15, wherein
the housing has a longer direction and a shorter direction perpendicular to the longer direction, and
the electrode member has a first electrode and a second electrode.

17. The non-burning type flavor inhaler according to claim 16, wherein
the electrode member includes an aperture allowing for communication between the housing cavity and an aerospace outside the housing, and
the aperture included in the electrode member is provided to be closer to a mouthpiece end side, in the longer direction, than a non-mouthpiece side end of either one of the first electrode or the second electrode.

18. The non-burning type flavor inhaler according to claim 16, wherein
the second electrode is spaced apart from the first electrode and provided internally of the first electrode, on a projection surface formed by light irradiated from the longer direction, the projection surface being formed on a surface perpendicular to the longer direction.

19. The non-burning type flavor inhaler according to claim 18, wherein
the electrode member has an aperture, and
the aperture is provided internally of the first electrode and externally of the second electrode, on the projection surface.

20. The non-burning type flavor inhaler according to claim 16, wherein
a non-mouthpiece side end of the second electrode is provided to be closer to a mouthpiece end side than a non-mouthpiece side end of the first electrode, in the longer direction.

21. The non-burning type flavor inhaler according to claim 1, wherein
the predetermined control other than the atomizing control is at least any one of: control for determining whether or not a user is an authorized user; control for starting or terminating a puff action series; control for switching an operation mode of the non-burning type flavor inhaler; control for resetting a value counted in the controller; and control for notifying a value managed by the controller.

* * * * *